(12) United States Patent
Ohara (10) Patent No.: US 7,027,556 B2
(45) Date of Patent: Apr. 11, 2006

(54) RADIATION IMAGE FORMATION SYSTEM

(75) Inventor: Hiromu Ohara, Hachioji (JP)

(73) Assignee: Konica Minolta Holdings, Inc., Tokyo (JP)

( * ) Notice: Subject to any disclaimer, the term of this patent is extended or adjusted under 35 U.S.C. 154(b) by 165 days.

(21) Appl. No.: 10/746,704

(22) Filed: Dec. 24, 2003

(65) Prior Publication Data

US 2004/0151277 A1 Aug. 5, 2004

(30) Foreign Application Priority Data

Dec. 27, 2002 (JP) .............................. 2002-379208

(51) Int. Cl.
 *G01N 23/04* (2006.01)

(52) U.S. Cl. ...................................... 378/62; 378/98.8

(58) Field of Classification Search .................. 378/62, 378/98.8, 87, 37

See application file for complete search history.

(56) References Cited

U.S. PATENT DOCUMENTS 6,222,906 B1 * 4/2001 Sakaguchi et al. ......... 378/98.8

* cited by examiner

*Primary Examiner*—David V. Bruce
*Assistant Examiner*—Hoon Song
(74) *Attorney, Agent, or Firm*—Squire, Sanders & Dempsey L.L.P.

(57) ABSTRACT

A radiation image formation system capable of reducing a magnified phase contrast image radiographed to life size and of outputting the reduced image at an output apparatus. The radiation image formation system has a magnified radiography setting unit for setting a magnifying rate M which satisfies:

magnifying rate M≦input pixel size A/minimum output pixel size B where the input pixel size A is a size of pixels composing a radiation image detected by a radiation image detector, and the minimum output pixel size B is a minimum size of pixels composing image data output by an image output apparatus, wherein a radiation image radiographing apparatus radiographs the radiation image at the magnifying rate M and an image process apparatus reduces the radiation image at the reducing rate 1/M.

17 Claims, 4 Drawing Sheets

RADIATION IMAGE FORMATION SYSTEM

BACKGROUND OF THE INVENTION

1. Field of the Invention

This invention relates to a radiation image formation system and, more particularly, to a radiation image formation system for reducing a magnified radiation image radiographed into life size and displaying the reduced radiation image.

2. Description of the Related Art

In recent years, a radiation image radiographing apparatus for radiographing a phase contrast image has been proposed. A phase contrast image is also called a refraction contrast image and used to be said that it could be obtained by radiographing with monochromatic parallel X-rays emitted from a synchrotron radiation X-ray source, such as Spring-8, or with a micro focus X-ray source having a focus size of about 10 μm. However, it has turned out that a phase contrast image can be obtained with a medical X-ray source (see Japanese Patent Application Publication (Laid-Open) No. 2001-91479). A phase contrast image is sharper and more high-resoluted than an ordinary absorption contrast image.

Such a phase contrast image is obtained in the following way. A subject is located apart from a radiation image detector for detecting X-rays which transmit through the subject. When the subject is radiographed, X-rays which transmit through the subject are refracted and the density of X-rays inside of the border of the subject becomes low. On the other hand, the density of X-rays outside of the border of the subject becomes high because X-rays which do not transmit through the subject and X-rays which transmit through the subject overlap. As a result, an edge, which is the border of the subject, is enhanced.

By the way, when a subject located apart from a radiation image detector is radiographed, the size of a radiation image obtained is larger than that of the subject. However, it is convenient, for example, for a doctor who makes a medical diagnosis to use a radiation image in life size. Therefore, preferably, a subject is magnified and is radiographed to obtain a phase contrast image. After that, the image reduced at the reducing rate 1/M, which corresponds to the magnifying rate M, is output. By doing so, the image in life size is recorded on a recording medium with a recording device.

Conventionally, a radiation image formation system in which radiography is performed by the use of a radiation image radiographing apparatus where a distance between a subject platform and a radiation detector can be adjusted freely, a magnifying rate is calculated from the distance between the subject platform and the radiation detector and then an image is reduced on the basis of this magnifying rate and output to an image output apparatus, is disclosed as a radiation image formation system for forming a phase contrast image as an image in life size (see Japanese Patent Application Publication (Laid-Open) No. 2001-238871, Paragraph Nos. [0061],[0064], and [0065], FIG. 7, etc.).

With such a conventional radiation image formation system (see Japanese Patent Application Publication (Laid-Open) No. 2001-91479), however, relations among an input pixel size by which a radiation image is converted into digital image data, a minimum output pixel size by which an image output apparatus outputs an image, and a magnifying rate at which a radiation image is radiographed are not taken into consideration. Accordingly, radiographing may be performed at a magnifying rate which satisfies magnifying rate>input pixel size/minimum output pixel size In this case, since a reducing rate is limited by the minimum output pixel size, an image to be output cannot be reduced in life size.

For example, if the input pixel size is 200 μm and the minimum output pixel size is 100 μm, an image to be output can be reduced at a reducing rate up to 1/2. When a radiation image is radiographed at the magnifying rate of, for example, 2, if the radiation image to be output is reduced at the reducing rate of 1/2, an image in life size can be obtained. Therefore, if the input pixel size is 200 μm and the minimum output pixel size is 100 μm, an image in life size can be output by performing radiographing at the magnifying rate of 2 and by reducing a radiation image obtained at the reducing rate of 1/2. However, an image in life size cannot be obtained when radiography is performed at the magnifying rate of 4. This is because a radiation image radiographed cannot be reduced at a reducing rate of 1/4.

SUMMARY OF THE INVENTION

An object of the present invention is to provide a radiation image formation system capable of reducing a magnified phase contrast image radiographed to life size and of outputting the reduced image at an output apparatus.

In accordance with a first aspect of the present invention, a radiation image formation system comprises: a radiation image radiographing apparatus capable of radiographing a radiation image magnified by a radiation image detector for detecting radiation which transmits through a subject; an image process apparatus for generating image data from the radiation image radiographed by the radiation image radiographing apparatus; an image output apparatus for outputting the image data input from the image process apparatus; and a magnified radiography setting unit for setting a magnifying rate M which satisfies:

magnifying rate $M \leq$ input pixel size $A$/minimum output pixel size $B$ where the input pixel size A is a size of pixels composing the radiation image detected by the radiation image detector, and the minimum output pixel size B is a minimum size of pixels composing the image data output by the image output apparatus, wherein the radiation image radiographing apparatus radiographs the radiation image at the magnifying rate M; and the image process apparatus reduces the radiation image at a reducing rate 1/M.

According to the system, since a radiation image is radiographed at a magnifying rate M which satisfies:

magnifying rate $M \leq$ input pixel size $A$/minimum output pixel size $B$, it is always possible to reduce the radiation image at a reducing rate 1/M corresponding to the magnifying rate M, and output the radiation image to the image output apparatus. As a result, an image in life size can be obtained.

Preferably, the system of the first aspect of the present invention further comprises an informing device for informing of an error, wherein the magnified radiography setting unit controls the informing device to inform of the error in the case of the radiation image radiographing apparatus being unable to radiograph the radiation image at the magnifying rate M.

According to the system, the informing device informs of the error when the magnifying rate satisfies:

magnifying rate>input pixel size/minimum output pixel size

As a result, it is possible to prevent useless radiography from being performed.

Preferably, in the system of the first aspect of the present invention, the radiation image radiographing apparatus is a mammography apparatus, the mammography apparatus comprises: a radiation source; a subject platform placed so as to be faced to the radiation source for supporting the subject; and a detector holding unit for holding the radiation image detector for detecting the radiation which transmits through the subject supported by the subject platform, and the subject platform and the radiation image detector are placed so as to be capable of moving so that a distance between the radiation source and the radiation image detector is not less than 75 cm and a distance between the subject platform and the radiation image detector is not less than 15 cm.

According to the system, a sharper phase contrast image of a mamma radiographed at the magnifying rate M can be reduced at the reducing rate 1/M which corresponds to the magnifying rate M, and be output to the image output apparatus. As a result, an image of a mamma can be obtained in life size.

Preferably, in the system of the first aspect of the present invention, the radiation image radiographing apparatus comprises: a radiation source; a subject platform placed so as to be faced to the radiation source for supporting the subject; and a detector holding unit for holding the radiation image detector for detecting radiation which transmits through the subject supported by the subject platform, the subject platform and the radiation image detector are placed so as to be capable of moving so that a distance between the radiation source and the radiation image detector is not less than 100 cm and a distance between the subject platform and the radiation image detector is not less than 30 cm.

According to the system, a sharper phase contrast image of a subject radiographed at the magnifying rate M can be reduced at the reducing rate 1/M which corresponds to the magnifying rate M, and be output to the image output apparatus. As a result, an image in life size can be obtained.

Preferably, in the system of the first aspect of the present invention, the input pixel size A is within the range from 30 μm to 100 μm.

In accordance with a second aspect of the present invention, a radiation image formation system comprises: a radiation image radiographing apparatus capable of radiographing a radiation image magnified by a radiation image detector for detecting radiation which transmits through a subject; an image process apparatus for generating image data from the radiation image radiographed by the radiation image radiographing apparatus; an image output apparatus for outputting the image data input from the image process apparatus; and an image process unit for reconstituting the radiation image with a reconstitution pixel size C which satisfies:

reconstitution pixel size $C \geq$ minimum output pixel size $B \times$ magnifying rate $M$ where the magnifying rate M is a magnifying rate at which the radiation image radiographing apparatus radiographs the radiation image, and the minimum output pixel size B is a minimum size of pixels composing the image data output by the image output apparatus, wherein the image process apparatus reduces the reconstituted radiation image at a reducing rate 1/M.

According to the system, since the radiation image is reconstituted with a reconstitution pixel size C which satisfies:

reconstitution pixel size $C \geq$ minimum output pixel size $B \times$ magnifying rate $M$, the reconstituted radiation image can be output to the image output apparatus with the image reduced at the reducing rate 1/M which corresponds to the magnifying rate M always. As a result, an image in life size can be obtained.

Preferably, the system of the second aspect of the present invention further comprises an informing device for informing of an error, wherein the image process unit controls the informing device to inform of the error in the case of being unable to reconstitute the radiation image with the reconstitution pixel size C.

According to the system, the informing device informs of the error when the reconstitution pixel size satisfies:

reconstitution pixel size < minimum output pixel size × magnifying rate

As a result, it is possible to prevent useless radiography from being performed.

Preferably, in the system of the second aspect of the present invention, the radiation image radiographing apparatus is a mammography apparatus, the mammography apparatus comprises: a radiation source; a subject platform placed so as to be faced to the radiation source for supporting the subject; and a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 75 cm and a distance between the subject platform and the radiation image detector is not less than 15 cm.

Preferably, in the system of the second aspect of the present invention, the radiation image radiographing apparatus comprises: a radiation source; a subject platform placed so as to be faced to the radiation source for supporting the subject; and a detector holding unit for holding the radiation image detector for detecting radiation which transmits through the subject supported by the subject platform, the subject platform and the radiation image detector are placed so as to be capable of moving so that a distance between the radiation source and the radiation image detector is not less than 100 cm and a distance between the subject platform and the radiation image detector is not less than 30 cm.

In accordance with a third aspect of the present invention, a radiation image formation system comprises: a radiation image radiographing apparatus capable of radiographing a radiation image magnified by a radiation image detector for detecting radiation which transmits through a subject; an image process apparatus for generating image data from the radiation image radiographed by the radiation image radiographing apparatus; an image output apparatus for outputting the image data input from the image process apparatus; and a magnified radiography setting unit for selecting, in the case where the magnified radiography setting unit comprises a plurality of image output apparatuses outputting images having different minimum output pixel sizes from one another, one among the plurality of image output apparatuses which outputs an image with a minimum output pixel size B which satisfies:

minimum output pixel size $B \leq$ input pixel size $A$/magnifying rate $M$ where the input pixel size A is a size of pixels composing the radiation image detected by the radiation image detector, and the magnifying rate M is a magnifying rate at which the radiation image radiographing apparatus radiographs the radiation image, wherein the radiation image radiographing apparatus radiographs the radiation image at the magnifying rate M; the image process apparatus reduces the radiation image at a reducing rate 1/M; and the magnified radiography setting unit makes the selected image output apparatus output the radiation image.

According to the system, the magnified radiography setting unit selects an image output apparatus which outputs an image in minimum output pixel size B which satisfies minimum output pixel size $B \leq$ input pixel size $A$/magnifying rate $M$, and an image is output to the image output apparatus. Accordingly, a radiation image can always be reduced at the reducing rate 1/M which corresponds to the magnifying rate M, and be output to the image output apparatus. As a result, an image in life size can be obtained.

Preferably, the system of the third aspect of the present invention further comprises an informing device for informing of an error, wherein the magnified radiography setting unit controls the informing device to inform of the error in the case of being unable to select the image output apparatus which outputs an image with the minimum output pixel size B.

According to the system, the informing device informs of the error when the minimum output pixel size satisfies:

minimum output pixel size>input pixel size/magnifying rate

As a result, it is possible to prevent useless radiographing from being performed.

Preferably, in the system of the third aspect of the present invention, the radiation image radiographing apparatus is a mammography apparatus, the mammography apparatus comprises: a radiation source; a subject platform placed so as to be faced to the radiation source for supporting the subject; and a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 75 cm and a distance between the subject platform and the radiation image detector is not less than 15 cm.

Preferably, in the system of the third aspect of the present invention, the radiation image radiographing apparatus comprises: a radiation source; a subject platform placed so as to be faced to the radiation source for supporting the subject; and a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 100 cm and a distance between the subject platform and the radiation image detector is not less than 30 cm.

Preferably, in the system of the third aspect of the present invention, the input pixel size A is within the range from 30 µm to 100 µm.

In accordance with a fourth aspect of the present invention, a radiation image formation system comprises: a radiation image radiographing apparatus capable of radiographing a radiation image magnified by a radiation image detector for detecting radiation which transmits through a subject; an image process apparatus for generating image data by reducing the radiation image radiographed by the radiation image radiographing apparatus; and an image output apparatus for outputting the image data input from the image process apparatus, wherein the image process apparatus generates the image data by reducing the radiation image at a reducing rate 1/M obtained by performing a thinning process on the image data when the following inequality is satisfied:

minimum output pixel size $B$>input pixel size $A$/magnifying rate $M$ where the input pixel size A is a size of pixels composing the radiation image detected by the radiation image detector, the magnifying rate M is a magnifying rate at which the radiation image radiographing apparatus radiographs the radiation image, and the minimum output pixel size B is a minimum size of pixels composing the image data output by the image output apparatus.

According to the system, when the inequality:

minimum output pixel size $B$>input pixel size $A$/magnifying rate $M$ is satisfied, the thinning process is performed on the image data to obtain the reducing rate 1/M. Accordingly, an image reduced at the reducing rate 1/M can always be output to the output apparatus. As a result, an image in life size can be obtained.

Preferably, in the system of the fourth aspect of the present invention, the radiation image radiographing apparatus is a mammography apparatus, the mammography apparatus comprises: a radiation source; a subject platform placed so as to be faced to the radiation source for supporting the subject; and a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 75 cm and a distance between the subject platform and the radiation image detector is not less than 15 cm.

Preferably, in the system of the fourth aspect of the present invention, the radiation image radiographing apparatus comprises: a radiation source; a subject platform placed so as to be faced to the radiation source for supporting the subject; and a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 100 cm and a distance between the subject platform and the radiation image detector is not less than 30 cm.

Preferably, in the system of the fourth aspect of the present invention, the input pixel size A is within the range from 30 to 100 µm.

BRIEF DESCRIPTION OF THE DRAWINGS

The present invention will become more fully understood from the detailed description given hereinafter and the accompanying drawings which are given by way of illustration only and which thus are not intended as a definition of the limits of the present invention, and wherein.

EMBODIMENTS OF THE INVENTION

Hereinafter, embodiments of the present invention will be described with reference to FIGS. 1 to 4. However, the scope of the present invention is not limited to the examples shown in these figures. In the following, descriptions a word "X-ray" will be considered synonymous with a word "radiation".

First Embodiment

Figure 1:
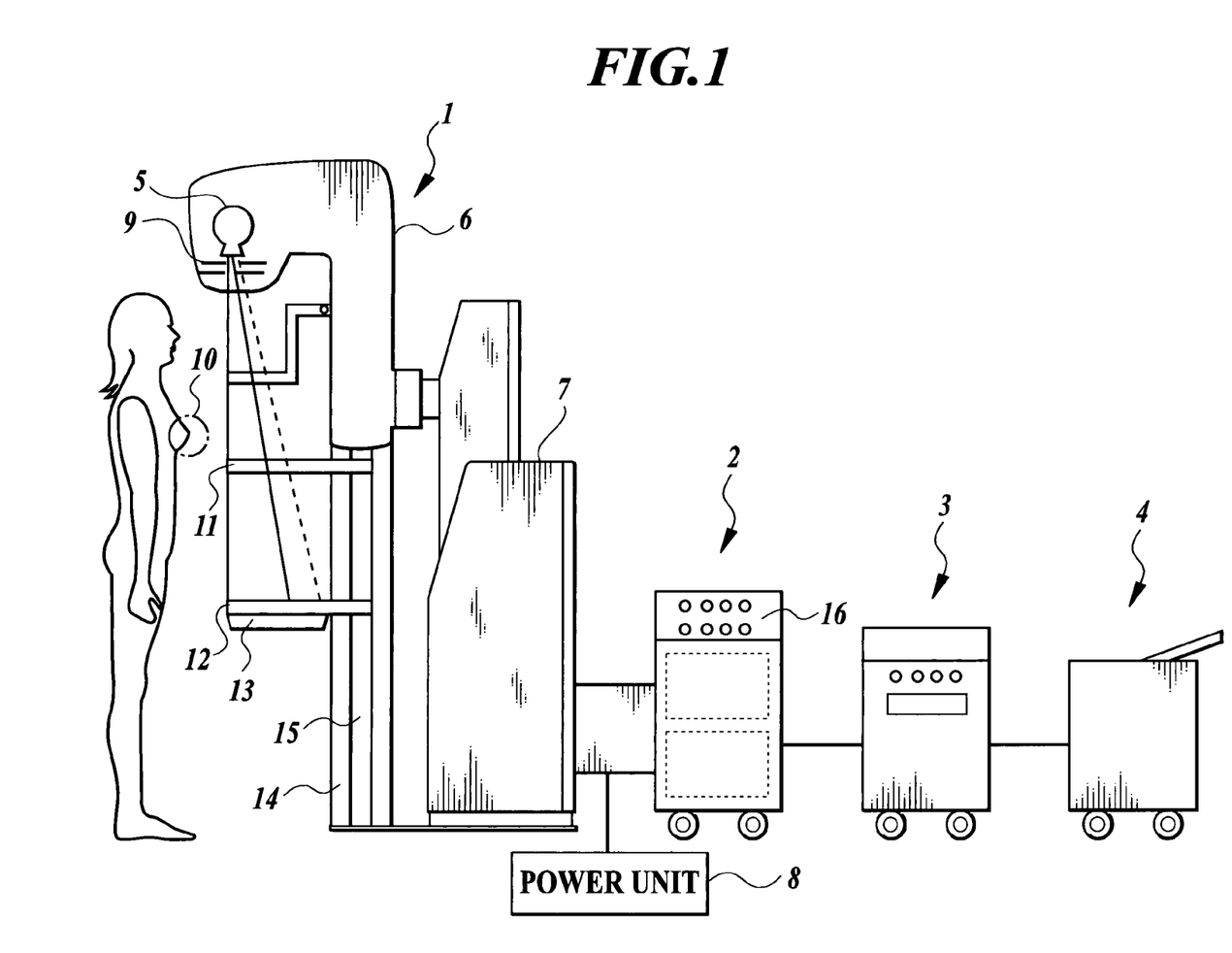
FIG. 1 is a view showing a structure of a radiation image formation system according to a first embodiment of the present invention.

A radiation image formation system according to the first embodiment of the present invention is used for forming a radiation image of a mamma. As shown in FIG. 1, such a radiation image formation system comprises a mammography apparatus 1 for radiographing a radiation image of a mamma, an operation apparatus 2 for performing operation regarding the radiography of a radiation image, an image process apparatus 3 for processing to convert a radiation image radiographed into digital image data, and an image output apparatus 4 for recording image data on a recording medium.

The mammography apparatus 1 comprises a body 6 in which a radiation source 5 is located. As shown in FIG. 1, the body 6 is supported by a supporting stand 7 so that the body 6 is capable of moving up and down. The radiation source 5 is connected to a power unit 8 for supplying electric power necessary for the radiation source 5 to emit radiation. At an irradiation gate of the radiation source 5, an aperture device 9 for adjusting an irradiation field is placed so that the aperture device 9 is capable of opening or closing.

An X-ray tube which emits X-rays with a wavelength of approximately 0.01 to 0.1 nm will be used as the radiation source 5. With such an X-ray tube, X-rays are emitted by converting kinetic energy, which is obtained by accelerating electrons generated by thermal excitation with high voltage and crashing them into an anode, into radiation energy. When an X-ray image is radiographed, the accelerating voltage is set as tube voltage, the number of electrons generated is set as tube current and X-ray emission time is set as exposure time. Copper, molybdenum, rhodium, tungsten or the like can be used for an anode (anticathode) into which electrons crash. The energy spectrum of emitted X-rays will vary according to material for the anode. If copper, molybdenum, rhodium or the like is used for the anode, a line spectrum having small range of X-ray energy distribution and comparatively low energy are obtained. These characteristics are used for crystal analysis by X-ray diffraction or mammography, which needs the interpretation of minute structures. If tungsten is used for the anode, X-rays having a broad spectrum and comparatively high energy are obtained. These characteristics are used for radiographing a chest, an abdomen or a head of a human body or industrial non-destructive inspection. An X-ray tube for medical or industrial purposes is characterized by large dose of X-rays. In this case, a large quantity of electrons crash into an anode at high speed, so the anode will overheat. If anode temperature rises, the anode may melt. Therefore, the anode should be rotated to change an area into which electrons crash. This can avoid a trouble caused from the overheating of the anode. In other words, generally a rotating anode is used. Since the radiographing apparatus according to the embodiment is used for medical purposes, it is preferable that an X-ray tube having a rotating anode made of molybdenum, rhodium or tungsten should be used. In addition, since the radiographing apparatus is the mammography apparatus 1, it is preferable that an X-ray tube having a rotating anode made of molybdenum or rhodium should be used.

Seen in a direction from a subject 10, a focal point of X-rays is a window for taking out X-rays generated by crashing electrons into, for example, a rotating anode in an X-ray tube. Generally, the window is a square and the length of its sides is a focal point size. If the shape of the window is a circle, its diameter is defined as a focal point size. If the shape of the window is a rectangle, the length of its shorter sides is defined as a focal point size. As a method for measuring a focal point size, a method with a pinhole camera, a method with a microtest chart and the like are stated in JIS Z 4704.

If the focal point size of X-rays becomes larger, larger dose of X-rays will be emitted. Accordingly, the so-called a half shadow will appear. A half shadow is a phenomenon where one point on the subject 10 is detected on a radiation image reading unit as an image of a certain size due to a focal point size, that is, unclearness. Therefore, unlike a synchrotron where monochromatic parallel X-rays are output nor a micro focus X-ray source where the focal point of X-rays can be regarded as a point, with an X-ray source having a focal point of small size, influence of the half shadow is problematic because of the focal point of limited size.

By the way, by radiographing the subject 10 with a radiation image detector apart from the subject 10, a phase contrast image on which the edge, which is the border part, of the subject 10 is enhanced because of X-rays transmitting through the subject 10 being refracted can be obtained. However, an increase in a distance between the subject 10 and the radiation image detector will result in an increase in the width of unclearness. Therefore, the lower limit of a focal point size is determined to obtain not less than certain dose of X-rays. In addition, the upper limit of a focal point size is determined from the distance between the subject 10 and the radiation image detector, the distance between the radiation source 5 and the subject 10, the physical properties of X-rays, or the like to obtain a sharp image by realizing a refraction contrast without causing unclearness. Accordingly, to radiograph a phase contrast image in ordinary medical facilities, a focal point size must be within the range from 30 to 300 μm, preferably from 50 to 200 μm.

A subject platform 11 on which the subject 10 is placed is located in an area below the radiation source 5 and within a radiation irradiation field. A detector holding unit 12 for holding the radiation image detector is located below the subject platform 11. A radiation dose detector 13 is located beneath the detector holding unit 12.

A photostimulable phosphor sheet, a radiation image detector where scintillators for converting X-ray energy into light and photo-semiconductor devices for reading the light are arranged two-dimensionally, a radiation image detector where scintillators for converting X-ray energy directly into electric signals and semiconductor devices for reading the electrical signals are arranged two-dimensionally, a radiation image detector where combinations of a scintillator for converting X-rays into light and a lens for concentrating the light on a CCD, a CMOS or the like are arranged two-dimensionally, or a radiation image detector where scintillators convert X-rays into light and the light is transmitted to CCD or CMOS through optical fibers for converting it into electrical signals may be used as the above radiation image detector.

A radiation image detector used for ordinary mammography is 18×24 cm or 24×30 cm in size. More preferably, the radiation image detector used for radiographing a phase contrast image is not less than 25×32 cm in size to obtain a magnified image. For convenience of handling a radiation image detector, the radiation image detector should be about 35×43 cm in size.

As shown in FIG. 1, the subject platform 11 and the detector holding unit 12 are supported by a slide axis 15 on a holding unit moving device 14, by which the detector holding unit 12 can be moved up and down. As a result, they are capable of sliding along the slide axis 15.

If radiography is performed with the distance between the radiation source 5 and the radiation image detector set to not less than 75 cm and the distance between the subject platform 11 and the radiation image detector set not less than 15 cm, a clear phase contrast image can be obtained. The wider the distance between the subject platform 11 and the detector holding unit 12 is, the more an edge effect from phase contrast becomes. However, if the distance is too wide compared to the distance between the radiation source 5 and the subject platform 11, sharpness of an image will be degraded due to unclearness of the half shadow. Therefore, preferably both the distance between the subject platform 11 and the detector holding unit 12 and the distance between the radiation source 5 and the subject platform 11 are wide in view of improving image quality. However, that will increase the whole size of the mammography apparatus 1. Therefore, problems will arise in view of the size of a radiographing room and convenience of handling the mammography apparatus 1.

From the above-mentioned viewpoints, preferably a range within which the detector holding unit 12 is capable of moving is determined so that the distance between the radiation source 5 and the detector holding unit 12 will be not less than 85 cm. On the other hand, for convenience of handling the apparatus, preferably a range within which the detector holding unit 12 is capable of moving is determined so that the distance between the radiation source 5 and the detector holding unit 12 will not be wider than 200 cm. In this case, to obtain a high-quality image, preferably the distance between the radiation source 5 and the subject platform 11 is within the range from 50 to 100 cm and the distance between the subject platform 11 and the detector holding unit 12 is within the range from 15 to 100 cm. More preferably, the distance between the radiation source 5 and the detector holding unit 12 is within the range from 90 to 165 cm, the distance between the radiation source 5 and the subject platform 11 is within the range from 60 to 75 cm, and the distance between the subject platform 11 and the detector holding unit 12 is within the range from 30 to 90 cm.

The power unit 8, the aperture device 9, the detector holding unit 12, the radiation dose detector 13, and the holding unit moving device 14 are connected to the operation apparatus 2 for performing operation regarding the formation of a radiation image.

Figure 2:
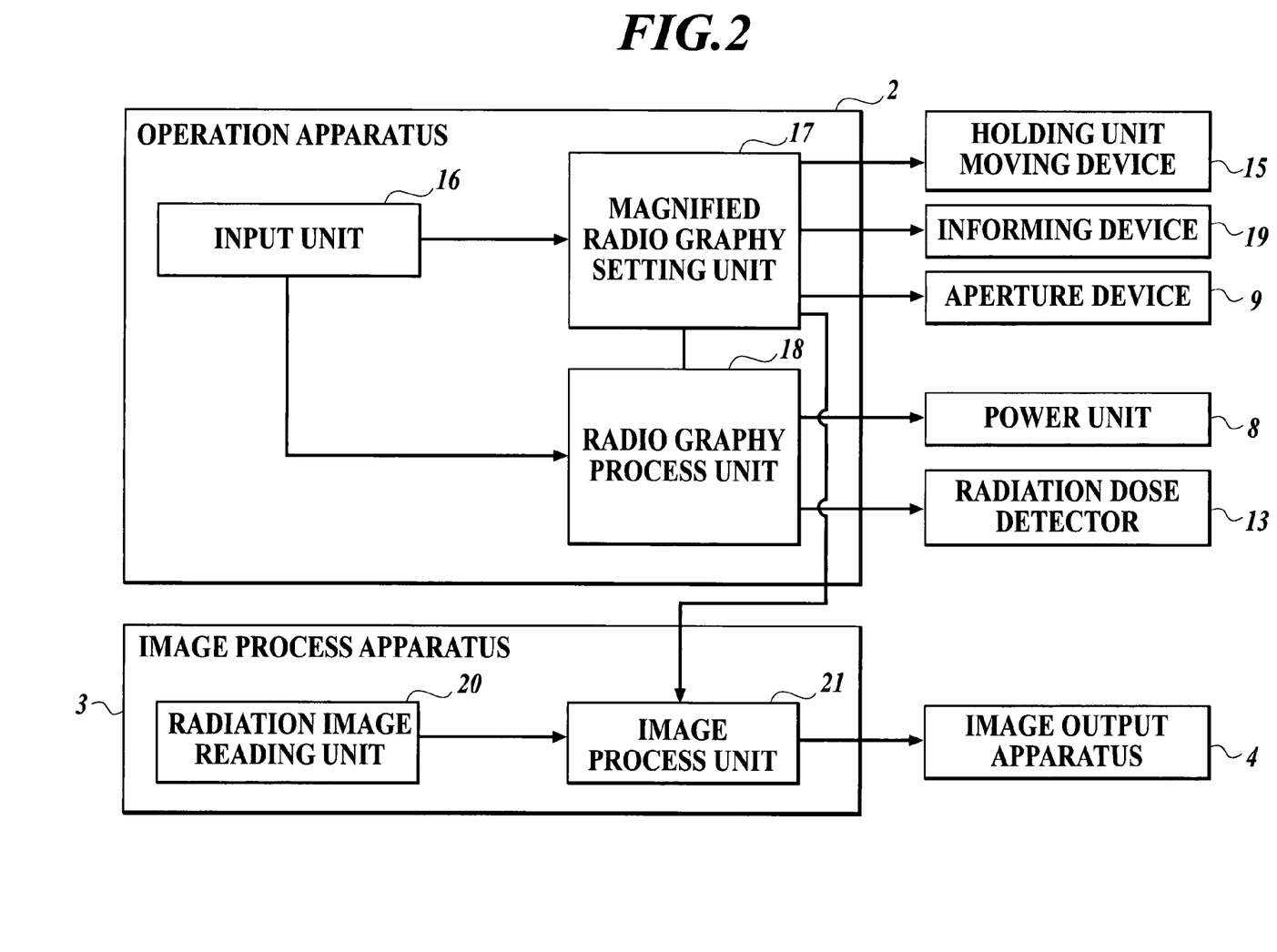
FIG. 2 is a block diagram showing the structure of a radiation image formation system according to one embodiment of the present invention.

The operation apparatus 2 comprises an input unit 16, such as a keyboard, a touch panel or the like, and the image output apparatus 4 for recording an image on a recording medium is connected to the operation apparatus 2. Moreover, as shown in FIG. 2, the operation apparatus 2 comprises a magnified radiography setting unit 17 for determining a magnifying rate at which an image is radiographed and a radiography process unit 18 for performing a process regarding the radiographing of a radiation image.

The magnified radiography setting unit 17 calculates magnifying rate M given by $$\text{magnifying rate } M = \text{input pixel size } A / \text{minimum output pixel size } B \qquad (1)$$

on the basis of the input pixel size A and the minimum output pixel size B input from the input unit 16.

An input pixel size is a size of the minimum unit elements which make up a radiation image detected by the radiation image detector and is determined by a size of semiconductor elements composing the radiation image detector for reading light or an electrical signal. If a photostimulable phosphor sheet is used as the radiation image detector, a laser beam scans the photostimulable phosphor sheet, radiation energy stored and recorded on the photostimulable phosphor sheet is emitted as light, and the intensity of the light is read as an electrical signal. Here, the input pixel size is determined from the size of the scanning unit of the laser beam (intervals on the radiation image detector at which electrical signals are read) or the size of semiconductor elements for reading an electrical signal. To obtain a high-resolution image, preferably the input pixel size is within the range from 30 to 300 μm. To radiograph an image of a mamma in particular, preferably the input pixel size is within the range from 30 to 100 μm.

A minimum output pixel size is a size of the minimum unit elements of image data which can be recorded on a recording medium by the image output apparatus. To obtain a high-resolution image, preferably the minimum output pixel size is within the range from 30/M to 300/M μm (M is a magnifying rate). To output an image of a mamma in particular, preferably the minimum output pixel size is within the range from 30/M to 100/M μm.

A magnifying rate is a ratio of the size of a radiation image compared to life size of the subject 10 and is determined from the distance between the radiation source 5 and the subject 10 and the distance between the subject 10 and the radiation image detector. Preferably magnifying rate is within the range from 1.2 to 3.0 in view of an edge effect on a phase contrast image and convenience of handling the mammography apparatus 1.

The magnified radiography setting unit 17 calculates the distance between the radiation source 5 and the radiation image detector, the distance between the radiation source 5 and the subject platform 11, and aperture amount of the aperture device 9 on the basis of the calculated magnifying rate.

Relations among the magnifying rate, the distance between the radiation source 5 and the radiation image detector, the distance between the radiation source 5 and the subject platform 11, and the aperture amount of the aperture device 9 are as follows. To obtain an image at the magnifying rate M given by equation (1), the distance between the radiation source 5 and the radiation image detector and the distance between the radiation source 5 and the subject platform 11 are necessary to be set so as to satisfy the ratio of an area on the radiation image detector on which radiation is irradiated compared to an area on the subject 10 on which radiation is irradiated being A to B. In addition, the aperture amount of the aperture device 9 must be set on the basis of the set distance between the radiation source 5 and the subject platform 11 so as to irradiate radiation on the entire subject 10 from the radiation source 5.

Then, the magnified radiography setting unit 17 controls the driving of the holding unit moving device 14 on the basis of the calculated distance between the radiation source 5 and the radiation image detector and the calculated distance between the radiation source 5 and the subject platform 11, locates the subject platform 11 and the detector holding unit 12 at predetermined positions and controls the opening and the closing of the aperture device 9 on the basis of the calculated aperture amount of the aperture device 9.

Moreover, if the calculated distance between the radiation source 5 and the radiation image detector or the calculated distance between the radiation source 5 and the subject platform 11 exceeds the range within which the subject platform 11 or the detector holding unit 12 is capable of moving, the magnified radiography setting unit 17 controls an informing device 19 so as to inform that proper magnified image radiographing cannot be set.

The radiography process unit 18 controls the power unit 8 on the basis of radiographing conditions such as dose, intensity of radiation the subject 10 and the like input from the input unit 16 so as to supply electric power necessary for the radiation source 5 to irradiate radiation. That is to say, the radiography process unit 18 controls the power unit 8 in response to a signal from the input unit 16 to make the radiation source 5 begin irradiating radiation having predetermined intensity. When the radiation source 5 begins irradiating radiation, the radiation dose detector 13 detects the dose of radiation which transmits through the subject 10. When the dose of radiation which transmits through the subject 10 reaches a predetermined value, the radiation dose detector 13 sends a signal to the radiography process unit 18. When the radiography process unit 18 receives the signal from the radiation dose detector 13, the radiography process unit 18 controls the power unit 8 to stop the radiation source 5 from irradiating radiation.

The image process apparatus 3 comprises a radiation image reading unit 20 and an image process unit 21.

Here, it is assumed that a photostimulable phosphor sheet is used as the radiation image detector. When a photostimulable phosphor sheet is inserted into the image process apparatus 3, the radiation image reading unit 20 makes a laser beam scan the photostimulable phosphor sheet. As a result, radiation energy recorded on the photostimulable phosphor sheet is emitted as light. The radiation image reading unit 20 reads the intensity of the excited light and converts it into an electrical signal.

The image process unit 21 accepts electrical signals corresponding to a radiation image directly converted by the radiation image detector or electrical signals corresponding to a radiation image processed and converted by the radiation image reading unit 20, and performs A/D conversion, a normalization process, a gradation process, and the like on the obtained electrical signals. In addition, the image process unit 21 accepts the magnifying rate M calculated by the magnified radiography setting unit 17 and generates image data reduced at the reducing rate 1/M, which corresponds to the magnifying rate M. Furthermore, the image process unit 21 may perform a frequency enhancement process, a dynamic range compression process and the like. The image process unit 21 outputs image data generated in such a way to the image output apparatus 4.

Next, operation of the embodiment will be described.

When an input pixel size and a minimum output pixel size are input from the input unit 16, the magnified radiography setting unit 17 calculates a magnifying rate M by the use of equation (1) and calculates a distance between the radiation source 5 and the radiation image detector, a distance between the radiation source 5 and the subject platform 11, and aperture amount of the aperture device 9 on the basis of the magnifying rate M. The magnified radiography setting unit 17 drives the holding unit moving device 14 on the basis of these calculated distances and locates the subject platform 11 and the detector holding unit 12 at predetermined positions. Moreover, the magnified radiography setting unit 17 opens or closes the aperture device 9 on the basis of the calculated aperture.

If these calculated distances exceed a range in which the subject platform 11 or the detector holding unit 12 is capable of moving, the magnified radiography setting unit 17 makes the informing device 19 inform that proper magnified image radiographing cannot be set.

Next, when the radiography process unit 18 accepts a signal from the input unit 16, the radiography process unit 18 controls the power unit 8 on the basis of radiographing conditions input from the input unit 16 to make the radiation source 5 begin irradiating radiation and makes the radiation dose detector 13 detect the dose of radiation which transmits through the subject 10. When the radiography process unit 18 receives a signal indicating that the dose of radiation which transmits through the subject 10 has reached a predetermined value from the radiation dose detector 13, the radiography process unit 18 controls the power unit 8 to stop the radiation source 5 from irradiating radiation.

In this case, an area on the radiation image detector where exposed to radiation which transmits through the subject 10 is M times larger than an area on the subject 10 where exposed to radiation.

The energy of radiation to which the radiation image detector is exposed is converted directly into an electrical signal by the radiation image detector, or is once stored and then converted into an electrical signal by having the radiation image reading unit 20 irradiate a laser beam and read the excited light therefrom.

Electrical signals corresponding to a radiation image are input to the image process unit 21. Then, the image process unit 21 performs an A/D conversion process, a gradation process and the like on the electrical signals to generate digital image data. The image data is reduced at the reducing rate 1/M, which corresponds to the magnifying rate input to the image process unit 21.

The reduced image data is output to the image output apparatus 4 and is recorded on a recording medium as an image in life size.

According to the present embodiment, the magnifying rate M is calculated on the basis of equation (1) and radiography is performed at the magnifying rate M. Therefore, an image of a mamma reduced at the reducing rate 1/M can be output to the image output apparatus and the image of the mamma can be obtained in life size. In addition, since the number of input pixels corresponds to that of output pixels, there is no need to perform an interpolation process. As a result, a highly accurate image of a mamma can be obtained.

Here, in the present embodiment, magnifying rate M is calculated by the use of equation (1). However, magnifying rate M may be calculated by the following inequality magnifying rate $M<$ input pixel size $A$/minimum output pixel size $B$     (2)

In this case, the magnified radiography setting unit 17 may omit a fraction of a value calculated by inequality (2) to obtain magnifying rate M. Alternatively, from among a plurality of magnifying rates set in advance, the magnified radiography setting unit 17 may select one that is the closest to a value calculated by inequality (2) as a magnifying rate M. The latter method can be used not only in a radiation image formation system according to the present embodiment where the subject platform 11 and the detector holding unit 12 are places so as to be capable of sliding freely, but also in a radiation image formation system where a plurality of detector holding units 12 are placed so as to select one of them.

If the magnifying rate M is calculated by the use of inequality (2), one input pixel is output by using a plurality of output pixels. For example, if four input pixels are displayed by nine output pixels, there are cases where one output pixel is located in a plurality of input pixels. In this case, an interpolation process, such as displaying an average value of a plurality of input pixels with one output pixel or the like, should be performed when an image is reduced by the image process unit 21 at the reducing rate 1/M, which corresponds to the magnifying rate.

In the present embodiment, magnifying rate M is calculated by the use of equation (1). However, a reconstitution pixel size C may be determined by the use of the following inequality reconstitution pixel size $C \geq$ minimum output pixel size $B \times$ magnifying rate $M$     (3)

The reconstitution pixel size is a size of a plurality of pixels which are unit elements of the radiation image detector and which are considered as one pixel by expressing them with one signal value obtained by averaging their signal values. For example, four pixels each of which is 40×40 µm in size can be considered as one pixel which is 80×80 µm in the reconstitution pixel size.

Moreover, by the use of the following inequality, the magnified radiography setting unit may select an image output apparatus for outputting an image by the minimum output pixel size B, and makes the selected image output apparatus output an image reduced at the reducing rate 1/M.

minimum output pixel size $B \leq$ input pixel size $A$/magnifying rate $M$     (4)

In addition, if the following inequality is satisfied, a thinning process and an interpolating process of image data at the reducing rate 1/M, which corresponds to magnifying rate M may be performed.

minimum output pixel size $B>$ input pixel size $A$/magnifying rate $M$     (5)

Figure 4A:
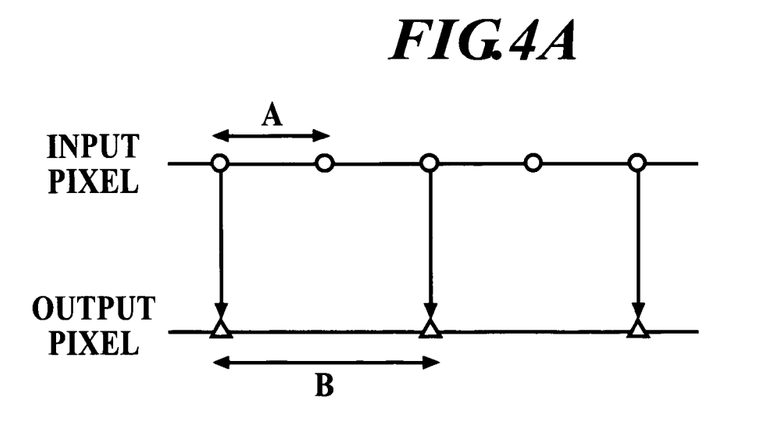
FIG. 4A is a simplified view showing an example of the thinning process.
Figure 4B:
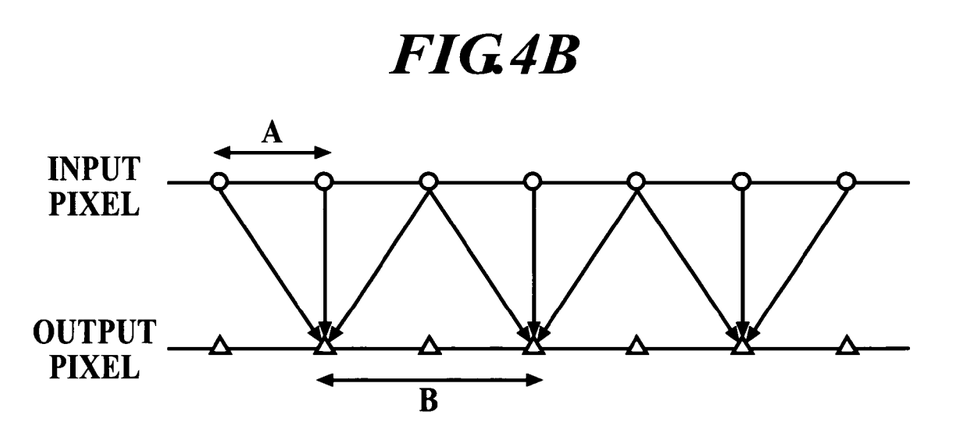
FIG. 4B is a simplified view showing an example of the thinning process and interpolating process.

For example, if both an input pixel size and minimum output pixel size are 80 µm, as shown in FIG. 4(A), in order to perform radiography at the magnifying rate 2, to reduce an image obtained at the reducing rate 1/2, and output the image in life size, one pixel in a line of the input pixels should be thinned out for every two pixels so that one output pixel is displayed at the end. Alternatively, as shown in FIG. 4(B), if one pixel in a line of the input pixels for every two pixels is displayed by one output pixel, data obtained by averaging the values of the pixel and two pixels adjacent thereto, or data obtained by performing a calculation on the basis of weight on the three pixels may be displayed by one output pixel.

Further, in the present embodiment, the image output apparatus 4 for recording an image on a recording medium is included. However, for example, a CRT display, a liquid crystal display or the like mounted on the operation apparatus 2 may be used as the image output apparatus 4.

In the present embodiment, the image process unit 21 is placed in the image process apparatus 3. However, the image process unit 21 may be placed in the operation apparatus 2. In addition, the operation apparatus 2 may be incorporated with the image process apparatus 3.

Further, in the present embodiment, an input pixel size, a minimum output pixel size and radiographing conditions, such as dose and intensity of radiation, are input from the input unit 16. However, information regarding radiographing an image may be stored in a server in advance, and then received via a network from the server for managing such information. By doing so, a position of the detector holding unit 12, aperture amount of the aperture device 9, a voltage value and dose of radiation are set automatically on the basis of the received input pixel size, minimum output pixel size, and radiographing conditions.

Here, in the present embodiment, the aperture device is included and the magnified radiography setting unit 17 calculates aperture amount to radiograph an image at a magnifying rate M given by equation (1) and controls the aperture device 9 on the basis of the aperture amount. However, aperture amount calculated by the magnified radiography setting unit 17 may be displayed on a display device such as a liquid crystal display or the like, and an irradiation field control plate having the aperture amount may be mounted.

Further, in the present embodiment, the subject platform 11 is supported by the slide axis 15 on the holding unit moving device 14 so as to be capable of sliding along the slide axis 15. However, the subject platform 11 may be fixed to the body 6 so that the distance between the radiation source 5 and the subject platform 11 is equal to a predetermined value. To obtain a phase contrast image, preferably the distance between the radiation source 5 and the subject platform 11 is within the range from 60 to 75 cm.

Second Embodiment

Next, a second embodiment of the present invention will be described. Here, components in the second embodiment having the same marks as those in the first embodiment have similar functions to the first embodiment.

Figure 3:
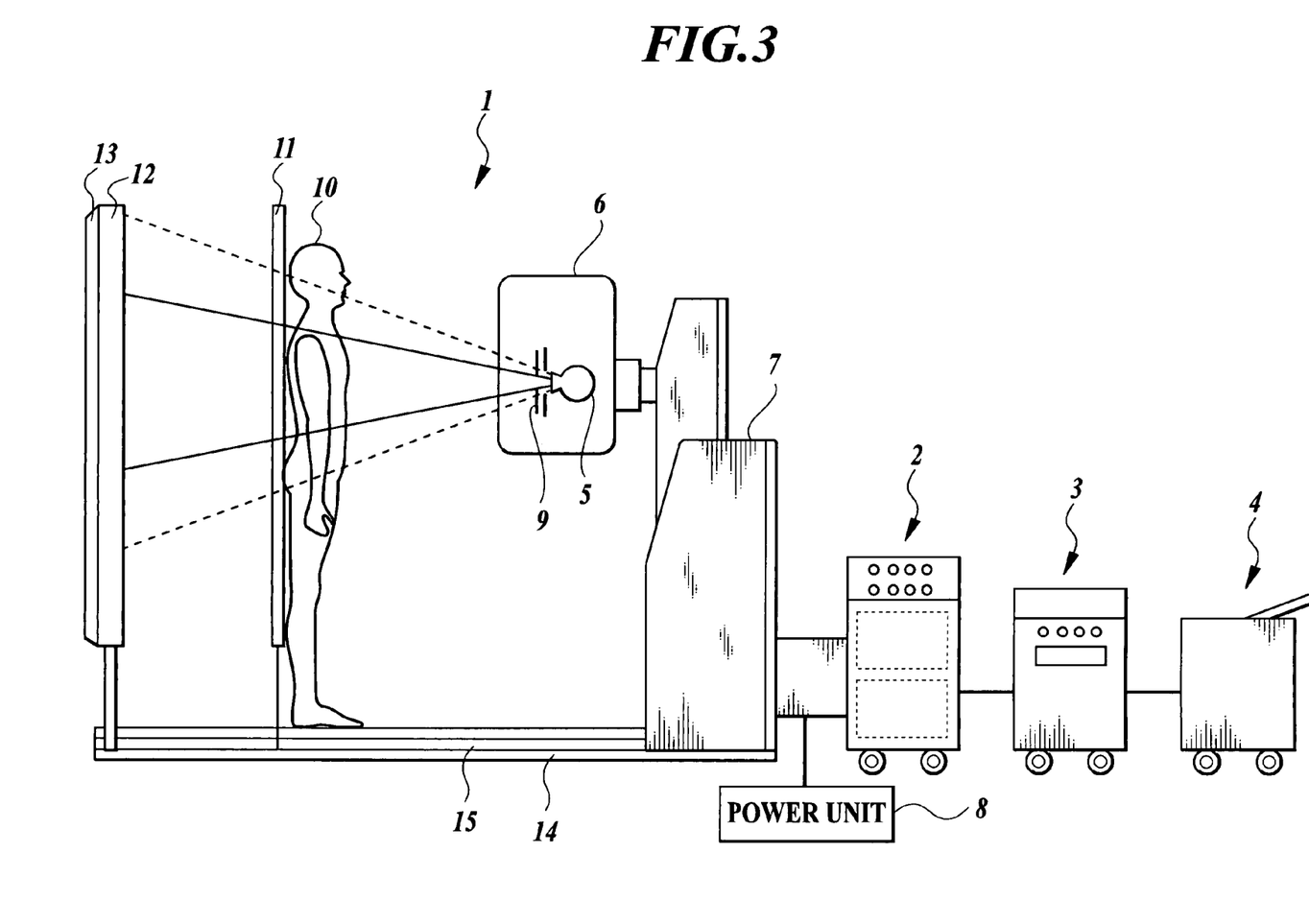
FIG. 3 is a view showing a structure of a radiation image formation system according to a second embodiment of the present invention.

A radiation image formation system according to the second embodiment of the present invention is used for forming a radiation image of a chest or the like. As shown in FIG. 3, such a radiation image formation system comprises a radiation image radiographing apparatus 1 for radiographing a radiation image of a chest or the like, an operation apparatus 2 for performing operation regarding the radiographing of a radiation image, an image process apparatus 3 for converting a radiographed radiation image into digital image data and an image output apparatus 4 for recording image data on a recording medium.

The radiation image radiographing apparatus 1 comprises a body 6 in which a radiation source 5 is located. As shown in FIG. 3, the body 6 is supported by a supporting stand 7 so as to be capable of moving up and down. The radiation source 5 is connected to a power unit 8 for supplying electric power necessary for the radiation source 5 to irradiate radiation. At an irradiation gate of the radiation source 5 an aperture device 9 for adjusting an irradiation field is placed so as to be capable of opening and closing freely.

A subject platform 11 for supporting a subject 10 is located within an area of radiation irradiation and at front in a direction of radiation irradiation from the radiation source 5. A detector holding unit 12 for holding a radiation image detector is located at front from the subject platform 11 in the direction of radiation irradiation. A radiation dose detector 13 is located on the back side of the detector holding unit 12.

The subject platform 11 and the detector holding unit 12 are supported by a slide axis 15, which moves the detector holding unit 13 toward right and left as shown in FIG. 3, on a holding unit moving device 14 so as to be capable of sliding along the slide axis 15. Here, if radiography is performed with the distance between the radiation source 5 and the radiation image detector set not less than 100 cm and the distance between the subject platform 11 and the radiation image detector set not less than 30 cm, a clear phase contrast image can be obtained.

Structures of the operation apparatus 2, the image process apparatus 3, and the image output apparatus 4 in the second embodiment are the same as those of the operation apparatus 2, the image process apparatus 3, and the image output apparatus 4, respectively, in the first embodiment.

According to the second embodiment of the present invention, a magnifying rate M is calculated on the basis of equation (1) and radiography is performed at the magnifying rate M. Therefore, an image of a chest reduced at the reducing rate 1/M can be output to the image output apparatus and an image of a chest can be obtained in life size. In addition, since the number of input pixels corresponds to that of output pixels, a highly accurate image of a chest can be obtained.

The present invention is not limited to the second embodiment. This is the same with the first embodiment.

The entire contents, including the specification, claims, drawings, and abstract, of Japanese patent Application No. 2002-379208 filed on Dec. 27, 2002 are incorporated herein by reference in their entirety.

What is claimed is:

1. A radiation image formation system comprising;
a radiation image radiographing apparatus radiographing a phase contrast radiation image magnified by a radiation image detector for detecting radiation which transmits through a subject located apart from the radiation image detector;
an image process apparatus for generating image data from the radiation image radiographed by the radiation image radiographing apparatus;
an image output apparatus for outputting the image data input from the image process apparatus; and
a magnified radiography setting unit for setting a magnifying rate M which satisfies:

magnifying rate $M \leq$ input pixel size $A$/minimum output pixel size $B$ where the input pixel size A is a size of pixels composing the radiation image detected by the radiation image detector, and the minimum output pixel size B is a minimum size of pixels composing the image data output by the image output apparatus,
wherein the radiation image radiographing apparatus radiographs the radiation image at the magnifying rate M; and the image process apparatus reduces the radiation image at a reducing rate 1/M.

2. The radiation image formation system of claim 1,
wherein the radiation image radiographing apparatus comprises:
a radiation source;
a subject platform placed so as to be faced to the radiation source for supporting the subject; and a detector holding unit for holding the radiation image detector for detecting radiation which transmits through the subject supported by the subject platform,
the subject platform and the radiation image detector are placed so as to be capable of moving so that a distance between the radiation source and the radiation image detector is not less than 100 cm and a distance between the subject platform and the radiation image detector is not less than 30 cm.

3. The radiation image formation system of claim 1,
wherein the input pixel size A is within the range from 30 μm to 100 μm.

4. A radiation image formation system comprising:
a radiation image radiographing apparatus radiographing a phase contrast radiation image magnified by a radiation image detector for detecting radiation which transmits through a subject located apart from the radiation image detector;
an image process apparatus for generating image data from the radiation image radiographed by the radiation image radiographing apparatus;
an image output apparatus for outputting the image data input from the image process apparatus; and
an image process unit for reconstituting the radiation image with a reconstitution pixel size C which satisfies:

reconstitution pixel size $C \geq$ minimum output pixel size $B \times$ magnifying rate $M$ where the magnifying rate M is a magnifying rate at which the radiation image radiographing apparatus radiographs the radiation image, and the minimum output pixel size B is a minimum size of pixels composing the image data output by the image output apparatus,
wherein the image process apparatus reduces the reconstituted radiation image at a reducing rate 1/M.

5. The radiation image formation system of claim 4,
further comprising an informing device for informing of an error,
wherein the image process unit controls the informing device to inform of the error in the case of being unable to reconstitute the radiation image with the reconstitution pixel size C.

6. The radiation image formation system of claim 4,
wherein the radiation image radiographing apparatus is a mammography apparatus, the mammography apparatus comprises:
a radiation source;
a subject platform placed so as to be faced to the radiation source for supporting the subject; and
a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 75 cm and a distance between the subject platform and the radiation image detector is not less than 15 cm.

7. The radiation image formation system of claim 4, wherein the radiation image radiographing apparatus comprises:
a radiation source;
a subject platform placed so as to be faced to the radiation source for supporting the subject; and
a detector holding unit for holding the radiation image detector for detecting radiation which transmits through the subject supported by the subject platform,
the subject platform and the radiation image detector are placed so as to be capable of moving so that a distance between the radiation source and the radiation image detector is not less than 100 cm and a distance between the subject platform and the radiation image detector is not less than 30 cm.

8. A radiation image formation system comprising:
a radiation image radiographing apparatus radiographing a phase contrast radiation image magnified by a radiation image detector for detecting radiation which transmits through a subject located apart from the radiation image detector;
an image process apparatus for generating image data from the radiation image radiographed by the radiation image radiographing apparatus;
an image output apparatus for outputting the image data input from the image process apparatus; and
a magnified radiography setting unit for selecting, in the case where the magnified radiography setting unit comprises a plurality of image output apparatuses outputting images having different minimum output pixel sizes from one another, one among the plurality of image output apparatuses which outputs an image with a minimum output pixel size B which satisfies:

minimum output pixel size $B$<input pixel size $A$/magnifying rate $M$ where the input pixel size A is a size of pixels composing the radiation image detected by the radiation image detector, and the magnifying rate M is a magnifying rate at which the radiation image radiographing apparatus radiographs the radiation image,
wherein the radiation image radiographing apparatus radiographs the radiation image at the magnifying rate M;
the image process apparatus reduces the radiation image at a reducing rate 1/M; and
the magnified radiography setting unit makes the selected image output apparatus output the radiation image.

9. The radiation image formation system of claim 8, further comprising an informing device for informing of an error,
wherein the magnified radiography setting unit controls the informing device to inform of the error in the case of being unable to select the image output apparatus which outputs an image with the minimum output pixel size B.

10. The radiation image formation system of claim 8, wherein the radiation image radiographing apparatus is a mammography apparatus, the mammography apparatus comprises:
a radiation source;
a subject platform placed so as to be faced to the radiation source for supporting the subject; and
a detector holding unit for holding the radiation image detector for detecting the radiation which transmits through the subject supported by the subject platform,
the subject platform and the radiation image detector are placed so as to be capable of moving so that a distance between the radiation source and the radiation image detector is not less than 75 cm and a distance between the subject platform and the radiation image detector is not less than 15 cm.

11. The radiation image formation system of claim 8, wherein the radiation image radiographing apparatus comprises:
a radiation source;
a subject platform placed so as to be faced to the radiation source for supporting the subject; and
a detector holding unit for holding the radiation image detector for detecting the radiation which transmits through the subject supported by the subject platform,
the subject platform and the radiation image detector are placed so as to be capable of moving so that a distance between the radiation source and the radiation image detector is not less than 100 cm and a distance between the subject platform and the radiation image detector is not less than 30 cm.

12. The radiation image formation system of claim 8, wherein the input pixel size A is within the range from 30 μm to 100 μm.

13. A radiation image formation system comprising:
a radiation image radiographing apparatus radiographing a phase contrast radiation image magnified by a radiation image detector for detecting radiation which transmits through a subject located apart from the radiation image detector;
an image process apparatus for generating image data by reducing the radiation image radiographed by the radiation image radiographing apparatus; and
an image output apparatus for outputting the image data input from the image process apparatus,
wherein the image process apparatus generates the image data by reducing the radiation image at a reducing rate 1/M obtained by performing a thinning process on the image data when the following inequality is satisfied:

minimum output pixel size $B$>input pixel size $A$/magnifying rate $M$ where the input pixel size A is a size of pixels composing the radiation image detected by the radiation image detector, the magnifying rate M is a magnifying rate at which the radiation image radiographing apparatus radiographs the radiation image, and the minimum output pixel size B is a minimum size of pixels composing the image data output by the image output apparatus.

14. The radiation image formation system of claim 13, wherein the radiation image radiographing apparatus is a mammography apparatus, the mammography apparatus comprises:
a radiation source;
a subject platform placed so as to be faced to the radiation source for supporting the subject; and
a detector holding unit for holding the radiation image detector for detecting the radiation which transmits through the subject supported by the subject platform,
the subject platform and the radiation image detector are placed so as to be capable of moving so that a distance between the radiation source and the radiation image detector is not less than 75 cm and a distance between the subject platform and the radiation image detector is not less than 15 cm.

15. The radiation image formation system of claim 13, wherein the radiation image radiographing apparatus comprises:

a radiation source;

a subject platform placed so as to be faced to the radiation source for supporting the subject; and a detector holding unit for holding the radiation image detector for detecting the radiation which transmits through the subject supported by the subject platform, the subject platform and the radiation image detector are placed so as to be capable of moving so that a distance between the radiation source and the radiation image detector is not less than 100 cm and a distance between the subject platform and the radiation image detector is not less than 30 cm.

16. The radiation image formation system of claim 13, wherein the input pixel size A is within the range from 30 to 100 μm.

17. A radiation image formation system comprising:

a radiation image radiographing apparatus radiographing a phase contrast radiation image magnified by a radiation image detector for detecting radiation which transmits through a subject located apart from the radiation image detector;

an image process apparatus for generating image data from the radiation image radiographed by the radiation image radiographing apparatus;

an image output apparatus for outputting the image data input from the image process apparatus; and a magnified radiography setting unit for selecting, in the case where the magnified radiography setting unit comprises a plurality of image output apparatuses outputting images having different minimum output pixel sizes from one another, one among the plurality of image output apparatuses which outputs an image with a minimum output pixel size B which satisfies:

minimum output pixel size $B$=input pixel size $A$/magnifying rate $M$ where the input pixel size A is a size of pixels composing the radiation image detected by the radiation image detector, and the magnifying rate M is a magnifying rate at which the radiation image radiographing apparatus radiographs the radiation image, wherein the radiation image radiographing apparatus radiographs the radiation image at the magnifying rate M; and the magnified radiography setting unit makes the selected image output apparatus output the radiation image.

* * * * *